US007618783B2

(12) United States Patent
Mangold et al.

(10) Patent No.: US 7,618,783 B2
(45) Date of Patent: Nov. 17, 2009

(54) ANTHRAX SPECIFIC ANTIBODIES

(75) Inventors: Beverly Lynn Mangold, Rockville, MD (US); Jennifer Lynn Aldrich, Silver Spring, MD (US); Thomas W. O'Brien, Fairfax, VA (US)

(73) Assignee: Tetracore, Inc., Rockville, MD (US)

( * ) Notice: Subject to any disclaimer, the term of this patent is extended or adjusted under 35 U.S.C. 154(b) by 157 days.

(21) Appl. No.: 09/844,281

(22) Filed: Apr. 30, 2001

(65) Prior Publication Data

US 2002/0082386 A1 Jun. 27, 2002

Related U.S. Application Data

(60) Provisional application No. 60/200,505, filed on Apr. 28, 2000.

(51) Int. Cl.
*G01N 33/53* (2006.01)
(52) U.S. Cl. .............................. 435/7.1; 435/4; 435/7.2; 435/7.32; 435/7.72; 435/975; 530/387.1; 530/388.1; 530/388.2; 530/388.4; 424/164.1
(58) Field of Classification Search ................. 435/975, 435/4, 7.1, 7.2, 7.32, 7.72; 530/387.1, 388.1, 530/388.2, 388.4
See application file for complete search history.

(56) References Cited

U.S. PATENT DOCUMENTS

| 5,840,312 A | 11/1998 | Mock et al. |
| 5,895,922 A | 4/1999 | Ho .......................... 250/491.2 |

FOREIGN PATENT DOCUMENTS

| WO | WO 86/02363 | 4/1986 |
| WO | WO 99/55842 | 11/1999 |
| WO | WO 99/64863 | 12/1999 |
| WO | WO 01/49823 | 7/2001 |

OTHER PUBLICATIONS

Kohler et al (Science. 1986. 233: 1281-1285).*
S. H. Leppla, "Anthrax Toxin Edema Factor: A Bacterial Adenylate Cyclase that Increases Cyclic AMP Concentrations in Eukaryotic Cells," *PNAS*, 79, 1982, pp. 3162-3166.
S.L. Welkos, et al., "Sequence and Analysis of the DNA Encoding Protective Antigen of *Bacillus anthracis*," *Gene*, 69, 1988, pp. 287-300.
V. Escuyer, et al., "Structural Homology Between Virulence-Associated Bacterial Adenylate Cyclases," *Gene*, 71, 1988, pp. 293-298.
T. S. Bragg, et al., "Nucleotide Sequence and Analysis of the Lethal Factor Gen (*lef*) from *Bacillus anthracis*," *Gene*, 81, 1989, pp. 45-54.
P. Matsudaira, "Sequence from Picomole Quantities of Proteins Electroblotted onto Polyvinylidene Difluoride Membranes," *J. Biol. Chem*, 262, 1987, pp. 10035-10038.
G. Long et al., "Antibody-Based Systems for the Detection of *Bacillus anthracis* in Environmental Samples," *Journal of Applied Microbiology*, vol. 87, No. 2, Aug. 1999, p. 214.
S. Mesnage et al., "Molecular Characterization of the *Bacillus anthracis* Main S-layer Component: Evidence that it is the Major Cell-Associated Antigen," *Molecular Microbiology*, vol. 23, No. 6, 1997, pp. 1147-1155.
A. Phillips et al., "Monoclonal Antibodies Against Spore Antigens of *Bacillus anthracis*," *FEMS Microbiology Immunology*, vol. 1, No. 3, Dec. 1988, pp. 169-178.
Ezzell, J.W., Jr., et al. "Immunological analysis of cell-associated antigens of *Bacillus anthracis*", *Infect Immun*. (1988) 56(2):349-56.
Phillips A.P., et al. "Identification of *Bacillus anthracis* by polyclonal antibodies against extracted vegetative cell antigens" *J Appl Bacteriol*. (1989) 66(5):419-32 (Abstract).
Farchaus, J.W., et al. "Purification and characterization of the major surface array protein from the avirulent *Bacillus anthracis* Delta Sterne-1", *J Bacteriol* (1995) 177(9):2481-9.

* cited by examiner

*Primary Examiner*—Jennifer E Graser
(74) *Attorney, Agent, or Firm*—Patentique PLLC (57) ABSTRACT

The present invention is directed to diagnostic tools and therapies using antibodies to *Bacillus anthracis*. Specifically, the present invention is directed to a *B. anthracis*-specific monoclonal antibody that binds to the EA1 antigen (corresponding to the eag gene) of the S-layer (surface layer) of spores. This monoclonal antibody may be used in a variety of applications, including to specifically detect and diagnose *B. anthracis*. Preferably, antibodies are monoclonal and bind to a surface protein, such as EA1 protein, on the spores of *B. anthracis*, and not to spores of either *B. cereus* or *B. thuringiensis*. Antibodies can be incorporated into detection kits using, for example, colloidal particle based lateral flow detection system. Such detection kits can distinguish anthrax spores from non-pathogenic varieties of spores. In addition, the invention is directed to *B. anthracis* EA1 antigen and pharmaceuticals such as vaccines that can be used as therapeutics and to develop improved antibodies and detection methods.

31 Claims, 2 Drawing Sheets

Figure 1

Amino Acid Sequence of Mature EA1 Protein
(without signal peptide)

```
             10         20         30         40         50         60
     AGKSFPDVPA GHWAEGSINY LVDKGAITGK PDGTYGPTES IDRASAAVIF TKILNLPVDE
             70         80         90        100        110        120
     NAQPSFKDAK NIWSSKYIAA VEKAGVVKGD GKENFYPEGK IDRASFASML VSAYNLKDKV
            130        140        150        160        170        180
     NGELVTTFED LLDHWGEEKA NILINLGISV GTGGKWEPNK SVSRAEAAQF IALTDKKYGK
            190        200        210        220        230        240
     KDNAQAYVTD VKVSEPTKLT LTGTGLDKLS ADDVTLEGDK AVAIEASTDG TSAVVTLGGK
            250        260        270        280        290        300
     VAPNKDLTVK VKNQSFVTKF VYEVKKLAVE KLTFDDDRAG QAIAFKLNDE KGNADVEYLN
            310        320        330        340        350        360
     LANHDVKFVA NNLDGSPANI FEGGEATSTT GKLAVGIKQG DYKVEVQVTK RGGLTVSNTG
            370        380        390        400        410        420
     IITVKNLDTP ASAIKNVVFA LDADNDGVVN YGSKLSGKDF ALNSQNLVVG EKASLNKLVA
            430        440        450        460        470        480
     TIAGEDKVVD PGSISIKSSN HGIISVVNNY ITAEAAGEAT LTIKVGDVTK DVKFKVTTDS
            490        500        510        520        530        540
     RKLVSVKANP DKLQVVQNKT LPVTFVTTDQ YGDPFGANTA AIKEVLPKTG VVAEGGLDVV
            550        560        570        580        590        600
     TTDSGSIGTK TIGVTGNDVG EGTVHFQNGN GATLGSLYVN VTEGNVAFKN FELVSKVGQY
            610        620        630        640        650        660
     GQSPDTKLDL NVSTTVEYQL SKYTSDRVYS DPENLEGYEV ESKNLAVADA KIVGNKVVVT
            670        680        690        700        710        720
     GKTPGKVDIH LTKNGATAGK ATVEIVQETI AIKSVNFKPV QTENFVEKKI NIGTVLELEK
            730        740        750        760        770        780
     SNLDDIVKGI NLTKETQHKV RVVKSGAEQG KLYLDRNGDA VFNAGDVKLG DVTVSQTSDS
            790        800        810        820        830        840
     ALPNFKADLY DTLTTKYTDK GTLVFKVLKD KDVITSEIGS QAVHVNVLNN PNL          (SEQ. ID. NO. 1)
```

Amino acids highlighted in red correspond to sequences determined for Bands 1 and 2.

ANTHRAX SPECIFIC ANTIBODIES

REFERENCE TO RELATED APPLICATIONS

This application claims priority to U.S. Provisional patent application No. 60/200,505, entitled "Anthrax Specific Antibodies," filed Apr. 28, 2000.

BACKGROUND OF THE INVENTION

1. Field of the Invention

This invention relates to antibodies to anthrax, and, in particular, to Bacillus species-specific antibodies that bind to the EA1 antigen of the S-layer, and to methods for making and using these antibodies. The invention further relates to kits that contain Bacillus species-specific antibodies for the rapid detection and identification of individual Bacillus species. The invention further relates to isolated EA1 antigen and compositions that contain the EA1 antigen for use as pharmaceuticals.

2. Description of the Background

Anthrax is a world wide disease of sheep, cattle, horses and other mammals caused by the spore-forming, saprophytic bacterium, *Bacillus anthracis*. Soil, the most common location of anthrax spores, typically becomes contaminated from the carcasses of infected animals that have died. Spores from the decaying carcasses are deposited in the soil, in the water and on vegetation. Like most types of spores, anthrax spores are very resistant to environmental changes such as extremes of heat and cold, and severe desiccation. Consequently, undisturbed spores can remain viable for decades.

Infection usually begins by entry of spores through injured skin or mucous membranes. Spores germinate at the site of entry and proliferate. Although not generally considered a respiratory pathogen, anthrax spores can initiate infection through the lungs. For example, Woolsorter's Disease, a rare from of anthrax, is caused by the inhalation of large quantities of anthrax spores from the dust of wool, hair or hides. Deep, concentrated inhalation results in the germination of spores in lung tissue and tracheobronchial lymph nodes. Unchecked, this disease is almost always fatal with symptoms which include the production of hemorrhagic mediastinitis, pneumonia, meningitis and sepsis. In anthrax sepsis, the number of organisms in the blood can exceed ten million per milliliter prior to death.

Most animals are susceptible to anthrax, but resistance is not uncommon (e.g. rat). In resistant animals, organisms proliferate for a few hours while also generating a massive accumulation of leukocytes. In these animals, dying organisms remain confined to capsules which gradually disintegrate and disappear. In susceptible animals, organisms germinate and rapidly proliferate at the site of entry. The most common portal of entry in animals is the mouth and the gastrointestinal tract. Spores within contaminated soil find easy access when ingested with spiny or other irritating vegetation. In humans, scratches of the skin and other injuries are the most likely routes of infection. Germination and growth of the vegetative organisms results in formation of a gelatinous edema and congestion with a generation of large amounts of proteinaceous fluid containing leukocytes. Bacilli spread via lymphatics to the bloodstream and multiply freely in blood and tissues shortly before death of the animal. In the plasma of animals dying from anthrax, a toxic factor has been identified. This factor kills mice upon inoculation and is specifically neutralized by anthrax antiserum.

Two factors are believed to be responsible for the toxic effect of anthrax infection; an edematogenic factor (EF) and a lethal factor (LF). These in combination with a membrane binding factor or protective antigen (PA), may have the capacity to confer active protection against disease (PNAS 79:3162-66, 1982). The genes which encode these protein factors (pag for PA, cya for EF, and lef for LF) have been cloned and sequenced (se Gene 69:287-300, 1988; Gene 71:293-98, 1988; and Gene 81:45-54, 1989). A recombinant strain of *B. anthracis* has been produced which is unable to produce LF or EF (U.S. Pat. No. 5,840,312). This strain has been used to create immunogenic compositions against anthrax infection.

Active immunity to anthrax can be induced in susceptible animals by vaccination with live attenuated bacilli, with spore suspensions, or with protective antigens from culture filtrates. Immunity is often incomplete and not long lasting so that the preferred treatment of choice is a course of antibiotics. If started early, antibiotic therapy has a high success rate.

As an acute, febrile disease of virtually all warm-blooded animals, including man, anthrax has been used in biological weapons. Terrorists have included dry spores in letters to target specific individuals for harassment. Biological weapons of mass destruction have been developed that contain large quantities of anthrax spores for release over enemy territory. Once released, spores contaminate a wide geographical area, infecting nearly all susceptible mammals. Due to the spore's resistance to heat and dry conditions, contaminated land can remain a danger for years. In view of the serious threat posed by the disease, effective diagnostic tools are needed to assist in prevention and control of natural and man-made outbreaks.

SUMMARY OF THE INVENTION

The present invention overcomes the problems and disadvantages associated with current strategies and designs and provides new compositions and methods for the detection and identification of anthrax.

One embodiment of the invention is directed to antibodies that are specifically reactive against spores of *B. anthracis*, and preferably not specifically reactive against *B. cereus* or *B. thuringiensis*. Antibodies may be of any isotype, such as IgA, IgD, IgE, IgG, IgM, or of any sub-type. Further, the invention also includes reactive fragments of these antibodies such as Fab or Fv fragments, or other antigenically active portions thereof. Antibodies may be directed to antigen on the surface of anthrax such as, for example, the EA1 antigen and, preferably, SEQ ID NO. 1, and fragments of this antigen or polypeptide. Anthrax-specific antibodies may be isolated and purified, polyclonal or monoclonal, or created by recombinant engineering techniques and include, for example, humanized antibodies.

Another embodiment of the invention is directed to a method of producing a species-specific monoclonal antibody to spores of one species of Bacillus such as, for example, *B. anthracis, B. cereus* or *B. Thuringiensis*. Preferably the method comprises immunizing a host with a preparation of Bacillus spores of on species, followed by boosting the host with spores of another species of the same genus, preferably an antigenically similar species. This boost, preferably at about seven days prior to fusion, stimulates clones that share specificity between the species of interest and the near neighbor so that, at the time of fusion, these clones will have diminished capacity to be fused. A second boost is administered to the host via, for example, an intravenous route (or intra peritoneal, subcutaneous, etc.), with the preparation of spores of interest from the target species. This second boost, preferably at about three days prior to fusion, stimulates clones that haven't already been stimulated by the antigenically similar boost such that the species-specific clones will be maximally susceptible to being fused. Antibody-producing cells are fused with immortalized cells and the anthrax specific hybridomas selected.

Another embodiment of the invention is directed to hybridomas that express Bacillus species-specific monoclonal antibodies such as anthrax-specific antibodies. These cell lines may be derived from nearly any mammal as well as other species such as, for example, cattle, chickens, goats, guinea pigs, horses, mice, pigs, primates, rabbits, rats and sheep.

Another embodiment of the invention is directed to diagnostic kits which incorporate Bacillus species-specific antibodies, and preferably anthrax-specific antibodies. Kits further contain a detection system such as, for example, a colloidal particle-based lateral flow system, a carbon-based lateral flow system, a fluorescent-based assay system, a chemiluminescent system, an up-converting phosphors system, a refractive index-based detection system, magnetic bead or latex bead systems, or a micro array system.

Another embodiment of the invention is directed to recombinant or isolated EA1 antigen from B. anthracis for use as a therapeutic. Recombinant or affinity purified EA1 antigen when, for example, combined with a pharmaceutically acceptable carrier, can be used as a therapy against the disease in a vaccine. Further, therapeutically effective doses of isolated or purified antibodies to the EA1 antigen, and active portions thereof, may also be effective in prophylaxis or treatment.

Other embodiments and advantages of the invention are set forth in part in the description which follows, and in part, will be obvious from this description, or may be learned from the practice of the invention.

DESCRIPTION OF THE INVENTION

As embodied and broadly described herein, the present invention comprises methods for the creation and use of antibodies that are specifically reactive against species of Bacillus such as, for example, B. anthracis, B. thuringiensis and B. Cereus. The invention further includes kits for the detection of individual Bacillus species such as B. anthracis and compositions that can be incorporated into vaccines and therapies to prevent or control disease.

Conventional methods for the detection of pathogenic infection by B. anthracis are slow and often subject to interpretation. These shortcoming can be directly attributed to an inability to distinguish pathogenic B. anthracis from closely-related, non-pathogenic species.

It has been discovered that identifiable epitopes exist that are unique to species of Bacillus such as, for example, B. anthracis. This surprising discovery was made by creating a species-specific antibody to anthrax, utilizing a procedure to maximize unique or distinguishing immunological features. One distinguishing feature of anthrax was found to be a surface protein, specifically the EA1 antigen, which is found in preparations of both spores and vegetative cells. By making the EA1 antigen of B. anthracis a preferred target for immunological detection, new diagnostic tools, therapies and treatments are available.

One embodiment of the invention is directed to species-specific antibodies to species of Bacillus such as, for example, antibodies that are specifically reactive against B. anthracis, B. thuringiensis or B. cereus. These antibodies may be monoclonal or polyclonal, recombinant or purified from natural sources, and be of any isotype such as IgA, IgD, IgE, IgG, or IgM, or any sub-type (e.g. IgG1, IgG2a, IgG2b). Purified antibodies may be obtained from infected animals and affinity purified, HPLC purified, or purified using other procedures known to those of ordinary skill in the art. Recombinant antibodies may be made from the genetic elements which encode anthrax-specific antibodies. These genetic elements can be expressed in a variety of systems, and large quantities of antibody, or active portions of antibodies, manufactured. Further, the invention includes reactive portions of any of these antibodies of the invention (e.g. Fab and Fv fragments), which may be used in isolation, in combination or in construction of recombinant antibodies such as, for example, humanized antibodies. Preferably, anthrax-specific antibodies are directed against the EA1 antigen, SEQ ID NO. 1, or antigenic parts of this antigen, such as a polypeptide having amino acids 181-833 of the EA1 protein.

Another embodiment of the invention is directed to a method of producing a species-specific monoclonal antibody to one species of Bacillus. This method preferably comprises first immunizing a host animal with a preparation of the species of interest such as, for example, B. anthracis, B. cereus or B. thuringiensis, which are all antigenically similar. Preparations may comprise spores, vegetative cells or combinations thereof. The host animal may be any animal suitable for the production of monoclonal antibodies such as, preferably, mice. Preferably about seven days prior to fusion, administering an intravenous boost using a preparation from another species of the same genus as the species used during the immunization. Preferably, this species are of an antigenically similar, but not identical, species. For example, when selecting for antibodies specific to B. cereus, either B. anthracis or B. thuringiensis may be used as the antigenically similar source. When selecting for antibodies specific to B. anthracis, either B. cereus or B. thuringiensis may be used as the antigenically similar source. This stimulates clones that share specificity between the species of interest and the near neighbor species. However, by the time of fusion about seven days later, these clones will have diminished capacity to be fused. Next, and preferably about three days prior to fusion, administering another boost via, for example, an intravenous route (intra peritoneal, subcutaneous, etc.), with a preparation of the species of interest. This stimulates clones that haven't already been stimulated by the antigenically similar boost, the specific clones. These species-specific clones should be maximally susceptible to being fused three days later. Thus, the number of cross-reacting clones should be greatly reduced or eliminated in the fusion products and a species-specific monoclonal antibody should be favored. Additional or fewer boosts may be performed and at various times to maximize generation of anthrax-specific hybridomas, as may be determined by one of ordinary skill in the art.

Antibody-producing cells are selected and fused with non-antibody producing cells such as, for example, immortalized cell lines. These fusion partners are typically transformed mouse cells such as myeloma cells of the mouse. After fusion, fused cells are segregated into individual cultures and propagated, and hybridoma lines which express anthrax-specific monoclonal antibodies are selected. Further, using these same methods and procedures, spore-specific and vegetative-specific epitopes can be identified and antibodies created. These cell lines can be maintain in culture or cryopreserved using techniques well known to those of ordinary skill in the art.

This general method can be used to select for species-specific antigens (and antibodies) between any two antigenically similar species whether they be spores, vegetative cells, viruses, phage, fungi, animal or plant cells, or any other types of microorganism.

Another embodiment of the invention is directed to hybridomas that express Bacillus species-specific monoclonal antibodies of the invention. These cell lines may be derived from nearly any mammal as well as other species such as, for example, cattle, chickens, goats, guinea pigs, horses, mice, pigs, primates, rabbits, rats and sheep. Preferably, the Bacillus species is anthrax and the hybridoma expresses anthrax-specific antibodies to aid in the detection of anthrax.

Another embodiment of the invention is directed to a diagnostic kit for the detection of individual species of Bacillus, such as, for example, anthrax. Anthrax, as well as non-pathogenic species of Bacillus, can be detected from, for example, spores and vegetative cells on nearly any material. For example, spores on any surface can be collected using conventional procedures (e.g. swipes, vacuums, washings) and tested.

Samples can also be taken from patients or the environment. Biological samples include, for example, liquids such as blood, plasma, urine, bile, cerebrospinal fluid, lymph fluid, amniotic fluid or peritoneal fluid. Tissues may also be tested and samples obtained from organs, skin, hair, fingernails or nearly any area of the body.

Environmental samples include, for example, samples collected from rivers and streams, salt or fresh water bodies, soil or rock, or samples of biomass. Detection kits comprise anthrax-specific antibodies or antibody fragments and a suitable detection system. The antibody or antibody fragment may be a whole antibody such as an IgG or an antibody fragment such as Fab or Fv fragment, or a minimum antigen-binding fragment. Detection kits may comprise solid supports for Bacillus or anthrax-specific antibodies, antigen or label, as appropriate. Suitable labels include, for example, radioactive labels, electromagnetic labels, electric field labels, fluorescent labels, enzyme labels, chemiluminescent labels, colored labels, and, preferably, visually perceptible labels. Detection systems may involve labeling the antibodies with a detectable label or a labeled secondary antibody that recognizes and binds to antigen-antibody complexes formed between, for example, anthrax spores and anthrax-specific antibodies of the invention. Preferably, the detectable label is visually detectable such as an enzyme, fluorescent chemical, luminescent chemical or chromatic chemical, which would facilitate determination of test results for the user or practitioner. Preferably the detection system is a colloidal particle based lateral flow detection system. Other detection systems include carbon based lateral flow system, a fluorescent based assay system, a chemiluminescent system, an up converting phosphors system, a refractive indexed based detection system, a magnetic bead or latex bead system, and a micro array system.

Diagnostic kits may further comprise agents to increase stability, shelf-life, inhibit or prevent product contamination and increase detection speed. Useful stabilizing agents include water, saline, alcohol, detergents, glycols including polyethylene glycol, oils, starches, sugars and polysaccharides, salts, glycerol, stabilizers, emulsifiers and combinations thereof. Useful antibacterial agents include antibiotics, bacterial-static and bacterial-toxic chemicals. Agents to optimize speed of detection may increase reaction speed such as salts and buffers. Using these procedures and components, kits can be created for the detection of anthrax. In addition, kits mat also be created for the detection on non-pathogenic strains of Bacillus. Such kits are useful as training tools and as controls in the detection of anthrax.

Figure 1:
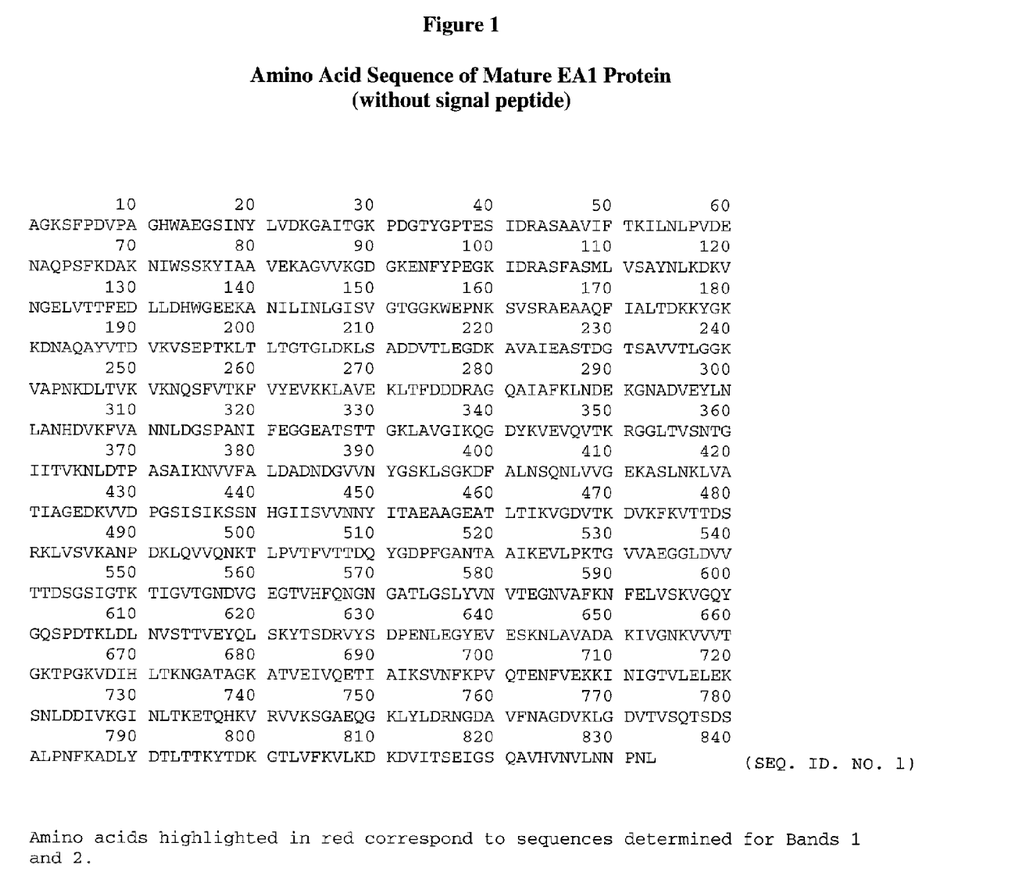
FIG. 1 Amino Acid sequence of mature EA1 protein (SEQ ID NO. 1).

Another embodiment of the invention is directed to an antigen comprising an EA1 antigen (corresponding to eag gene) of the S-layer (surface layer) of *B. anthracis* (FIG. 1). This antigen is found in both spore and vegetative cell preparations of anthrax and can be isolated and purified, for example, using affinity chromatography. The corresponding gene can also be cloned and sequenced. As a unique antigenic marker for pathogenic anthrax, this protein may be used as a therapeutic pharmaceutical or vaccine to prevent infection.

Another embodiment of the invention is directed to a therapeutic vaccine against *B. anthracis* comprising the EA1 antigen and/or monoclonal or polyclonal antibodies to the EA1 antigen (i.e. anti-EA1-antibodies), and a pharmaceutically acceptable carrier. The entire protein (antibody or antigen), or an active portion thereof, can be used to vaccinate susceptible individuals to prevent or treat an infection. Antibodies provide passive immunity, most useful as treatment after exposure, and antigens provide active immunity for long term protection and prophylaxis. Preferably, antigens stimulate the immune system to create a cellular and/or antibody response in the individual vaccinated. Another embodiment of the invention is directed to a method for vaccinating against *B. anthracis* comprising administering the EA1 antigen or anti-EA1 antibody to a patient. The invention also includes therapeutic agents comprising antibodies to the EA1 protein and to methods for treating, preventing or controlling *B. anthracis* infection comprising administering an effective amount of antibodies to the EA1 antigen to a patient.

The following examples illustrate embodiments of the invention, but should not be view as limiting the scope of the invention.

EXAMPLES

Immunizations

Balb/c mice were immunized subcutaneously with *B. anthracis* spores prepared from the Sterne vaccine strain at three to four week intervals for up to five months. The first immunization was with 200 ug antigen in Freund's complete adjuvant. Subsequent boosts were with 100 ug antigen in Freund's incomplete adjuvant. Seven days prior to the fusion, mice were injected intravenously (iv) with 5 ug *B. thuringiensis* spores, of the A1 Hakam and HD-571 strains (obtained from Los Alamos National Laboratories) combined into one antigen preparation. Seventy-two hours prior to the fusion, mice were immunized iv with 5 ug *B. anthracis* spores in PBS. Mouse sera was tested by direct ELISA after the third boost, and periodically after that to test antibody titers to *B. anthracis* spores.

Fusions

Hybridoma cells were developed to *B. anthracis* spores by fusion of nonsecreting myeloma cells (SP2/0) with antibody-producing B-lymphocytes from the spleens of mice immunized with *B. anthracis* spores, in the presence of polyethylene glycol (PEG), according to standard hybridoma procedures. Cells were combined in a ratio of 3:1 (spleen: myeloma), and fused with PEG. Fused cells were plated, and cultured in 96-well cell culture grade plates. Fused cells were then selected by addition of HAT media [Iscove's Modified Dulbecco's Media (IMDM) with HAT supplement containing hypoxanthine, aminopterin, and thymidine]. These HAT supplements select for the fused hybridoma cells, and eliminate unfused or self-fused myeloma cells. Once clones appeared in the wells (usually 7-10 days after fusion), the culture supernatants were screened by ELISA for antibodies to *B. anthracis* spores. Positive antibody producing cells were subcloned by serial dilution, and plated at a cell concentration of three cells per well, and then further at one cell per three wells in a 96-well culture plate. This was performed with ten percent ORIGIN® Hybridoma Cloning Factor (HCF) in IMDM. Between each cloning step, culture supernatants were screened by ELISA for antibody production. Finalized clones were screened for isotype, and cryopreserved in liquid nitrogen. Two fusions were performed resulting in the generation of numerous monoclonal antibodies to *Bacillus anthracis* (Table 1).

ELISA Screening

Cell supernatants were screened by direct ELISA. ELISA plates were coated with *B. anthracis* spore and vegetative preparation antigens as positive antigen, and bovine serum albumin (BSA) as negative antigen, diluted to an optimized concentration in PBS. Plates were incubated 18-24 hours at 4° C. Plates were washed four times with PBS. Cell supernatants were added to both positive and negative coated antigen wells, undiluted. Mouse sera from the immunized mice was added to plate at a dilution of 1:200, and serially diluted to an endpoint. This was included as a positive control. Plates were incubated at 37° C. for one hour. Plates were washed four times with PBS. Horseradish peroxidase (HRP) conjugated goat anti mouse IgG+M+A (KPL) was added to all wells, and incubated at 37° C. for one hour. Plates were washed four times with PBS. Substrate was added to plates and incubated at 37° C. for 30 minutes. Plates were read for optical density at 280 nm, and evaluated for positive results. Cells producing the highest optical density readings, i.e., above 1.000 OD, were subcloned. After each subcloning, cell supernatants were screened for positive antibody. Finalized clones were tested for isotype using monoclonal antibody-based mouse Ig isotyping kit (catalog # 04017K; BD PharMingen). Three monoclonal antibodies (termed AX-EA1-G1, 8G4, and 9F5) were selected for their ability to uniquely detect *B. anthracis* and not cross-react with other closely related Bacillus species. Monoclonal antibody AX-EA1-G1 was deposited with the ATCC (10801 University Blvd., Manassas, Va., 20110-2209) and accorded accession number PTA-2632, on Oct. 26, 2000. The selection of these monoclonal antibodies was based on their strong reactivity against *B. anthracis* antigens and their negative reactivity against the closely related strains of *B. thuringiensis* (ATCC 33680, HD571, A1 Hakam, and commercial insecticide preparation from Dipel Dust), *B. globigii* and *B. licheniformis* (ATCC 25972) (Table 2, 3 and 4). In addition, these monoclonal antibodies were negative when tested against a selected number of other bacteria (*Francisella tularensis* and *Yersinia pestis*), purified proteins (ovalbumin and *S. aureus* enterotoxin B), and environmental components (red clay, gravel, and mulch) (Table 2, 3 and 4).

Specificity Testing

To test for cross-reactivity, an antigen capture ELISA was performed. Plates were coated with rabbit anti-anthrax IgG antibody as positive capture, and normal rabbit IgG as negative capture antibody. Plates were incubated overnight at 4° C. Plates were washed four times with PBS and then blocked with dry skim milk buffer. Plates were incubated for one hour at 37° C., and washed four times with PBS. Antigens were added to both positive and negative antibody coated wells at concentrations determined for cross-reactivity analysis. Plates were incubated for one hour at 37° C., and washed four times with PBS. Monoclonal antibodies (Mabs) were added to the plate at optimized concentrations, as detector antibodies. Plates were incubated for one hour at 37° C., and washed four times with PBS. Anti-species conjugate was added to the plate. Plates were incubated for one hour at 37° C., and washed four times with PBS. Substrate solution was added to the plate, and incubated for 30 minutes at 37° C. Plates were read at 280 nm for optical density readings.

Identification and Affinity Purification of *B. anthracis* antigen

An affinity column was made using the anthrax-specific monoclonal antibody AX-EA1-G1 complexed to the Immunopure Protein G IgG Orientation Kit (Pierce; Rockford, Ill.), according to manufacture's protocol. An anthrax spore antigen preparation was affinity purified over the column using the manufacturer's protocol.

SDS PAGE and Electroblotting

Affinity-purified anthrax antigens under went electrophoresis by SDS-PAGE on a 4-15% Tris-HCl polyacrylamide Ready Gel Precast Gel in a Mini-Protean 3 Electrophoresis Cell (Bio-Rad; Hercules, Calif.). Specifically, affinity-purified anthrax antigens (5.7 ug total), along with tubes containing molecular weight markers, were diluted in sample buffer (62.5 mM Tris-HCl pH 6.8, 2% SDS, 25% glycerol, 0.01% Bromophenol blue), boiled for 2.5 minutes, loaded onto the 4-15% gel and under went electrophoresis at 200V for 30 minutes.

The electroblotting procedure was performed according to the protocol posted on the Michigan State web site (http://gaea.bch.msu.edu/mssef/blotting.html) by the method of Matsudaira (J Biol Chem, 1987, 262:100035). Briefly, a 0.2 um PVDF membrane (Sequi-Blot PVDF Membrane for Protein Sequencing; Bio-Rad) was wet with methanol, soaked in CAPS/methanol buffer, electroblotted in a Mini Trans-Blot Electrophoresis Transfer Cell (Bio-Rad) at 50 V for one hour, according to manufacturer's instructions, in CAPS/methanol buffer.

The blotted PVDF membrane was stained with 0.2% Amido Black in 40% methanol for 40 seconds and destained in $dH_2O$. Two bands, of approximate molecular weight of 97 kD ("Band 1") and 62 kD ("Band 2"), were visualized.

Protein Sequencing

Monoclonal antibody AX-EA1-G1 was used to affinity purify the specific *B. anthracis* antigen that the antibody was detecting. The affinity-purified antigen(s) was separated on by SDS-PAGE and electroblotted onto a PVDF membrane. Two bands were visualized after staining at approximate molecular weights of 97 kD (Band 1) and 62 kD (Band 2); the membrane was sent to the Biotechnology Center of Utah State University for protein sequencing. The amino acid sequence was determined to be:

```
Band 1: A G K Z F P Z V P A G H (SEQ ID NO 2)

Band 2: D Z K Z N A Q A Y V T D (SEQ ID NO 3)
(Z = uncertain amino acid)
```

Using both of these amino acid sequences, a tblastn protein search of the Unfinished Microbial Genomes TIGR database of *B. anthracis* sequences was performed. An exact match was observed with the definitive amino acid sequences for Contig 1819. A BLAST search of GenBank using the nucleotide sequence of contig 1819 resulted in complete homology to the eag gene that codes for the EA1 protein of the *B. anthracis* S-layer. The amino acid position corresponding to the sequence of Bands 1 and 2 are illustrated in FIG. 1. Since the AX-EA1-G1 monoclonal antibody bound to both bands, it can be concluded that the epitope to which AX-EA1 -G1 binds is located somewhere within amino acids 181-833.

Competitive Inhibition Analysis

To determine whether the monoclonal antibodies produced to *B. anthracis* compete for the same epitope(s), a competitive inhibition assay was performed. ELISA plates were coated with rabbit anti-anthrax IgG as positive capture antibody, and normal rabbit IgG as negative capture antibody. Plates were incubated overnight at 4° C. Plates were washed four times with PBS and then blocked with dry skim milk buffer. Plates were incubated for one hour at 37° C., and washed four times with PBS. Antigens were added to both positive and negative antibody coated wells at concentrations determined for inhibition analysis. Plates were incubated for one hour at 37° C., and washed four times with PBS. Three separate monoclonal antibodies were used in the competition at the detector antibody step. One Mab, labeled with biotin, was held constant while the other Mabs were unlabeled and combined separately at different concentrations, with the biotin labeled Mab. Each combination was prepared in a micro-tube rack, and then added to the plate at the same time. Plates were incubated for one hour at 37° C., and washed four times with PBS. Conjugated streptavidin was added to the plates and incubated for one hour at 37° C. Plates were washed and substrate solution added. Plates were incubated for 30 minutes, and read for optical density at 280 nm.

Figure 2:
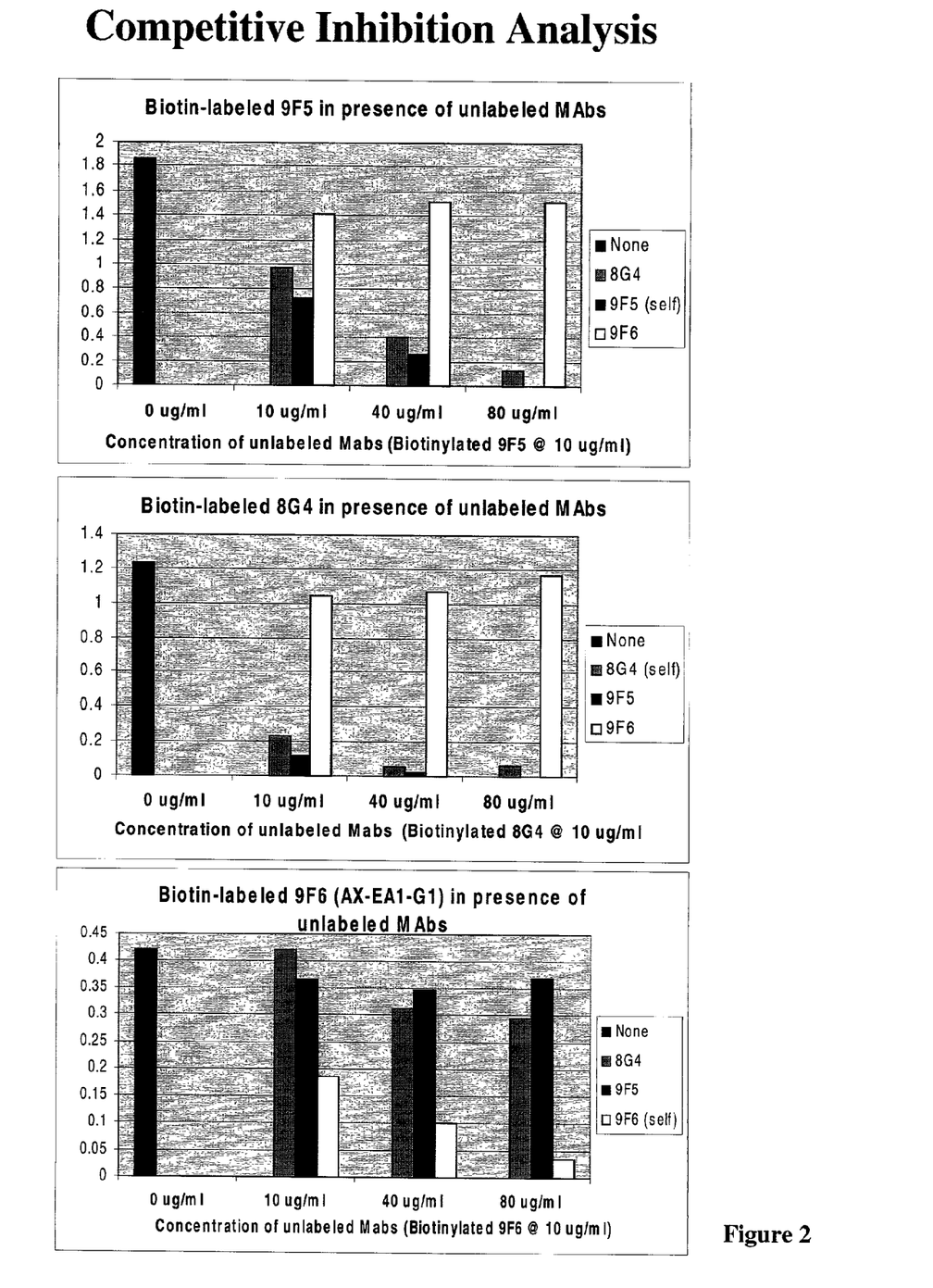
FIG. 2 Competitive inhibition assays of anthrax-specific antibodies.

Having determined that the monoclonal antibody AX-EA1-G1 reacts with the EA1 protein of *B. anthracis*, the other two monoclonal antibodies, 8G4 and 9F5, were tested against affinity-purified antigen and shown to also react with the EA1 antigen (Table 1). Therefore, all three monoclonal antibodies were shown to bind to the same EA1 protein. However, competitive inhibition analysis revealed that while 8G4 and 9F5 effectively compete for binding to the same epitope on the EA1 protein as each other, AX-EA1-G1 does not compete with the binding of 8G4 and 9F5 and therefore binds to a different epitope on the EA1 protein (FIG. 2).

Other embodiments and uses of the invention will be apparent to those skilled in the art from consideration of the specification and practice of the invention disclosed herein. All references cited herein, including all U.S. and foreign patents and patent applications and U.S. Provisional Pat. No. 60/200,505, are specifically and entirely hereby incorporated herein by reference. It is intended that the specification and examples be considered exemplary only, with the true scope and spirit of the invention indicated by the following claims.

TABLE 1

Relative Scoring of ELISA Data Based on 0-3 Scale*

| Antibody | Form | Isotype | Sp1** | Sp3 | SpG1 | SpG3 | V1 | V + M |
|---|---|---|---|---|---|---|---|---|
| 1- 9F6 (AX-EA1-G1) | Purified | IgG1 | P/M | 3 | 3 | 3 (+) | 2 | 3 |
| 7- 8G4- 1D7 | Purified | IgG1 | 2 | 3 | 3 (+) | 3 | 3 (+) | 3 |
| 7- 3C3- 2C2 | Purified | IgG1 | P/M | 3 | 2 | 1 | 2 | 3 |
| 7- 1D4- 1G7 | Purified | IgG1 | 1 | 3 | 2 | 3 | 3 | 3 |
| 7- 6B6- 1C9 | Purified | IgG1 | 0 | 1 | 2 | 1 | 3 | 3 |
| 7- 1E10- 1B5 | Purified | IgG1 | 0 | 1 | 2 | 1 | 3 | 2 |
| 7- 9F5- 2B11 | Purified | IgG1 | 1 | 3 | 3 (+) | 3 | 3 | 3 |
| 7- 9C2- 1C11 | Purified | IgG1 | 1 | 3 | 2 | 3 | 3 | 3 |
| 7- 5E4- 1C10 | Purified | IgG1 | 1 | 3 | 2 | 1 | 2 | 3 |
| 7- 8D3- 1E6 | Cell sup | IgG1 | 0 | 1 | 0 | 0 | 1 | P/M |
| 7- 2B11- 1B10 | Cell sup | IgG1 | 1 | 3 | 2 | 2 | 3 | 3 |
| 7- 7E10- 1D8 | Cell sup | IgG1 | 0 | P/M | P/M | P/M | 2 | 1 |
| 7- 9E8- 1B11 | Cell sup | IgG1 | 2 (+) | 3 | 3 | 3 | 3 | 3 |
| 7- 10E8 | Cell sup | IgG1 | 1 | 3 | 3 (+) | 3 | 2 | 3 |
| 7- 1G7- 1A6 | Cell sup | IgG1 | 1 | 3 | 3 | 1 | 2 | 3 |
| 7- 8D7 | Cell sup | IgG1 | 1 | 3 | 2 | 2 | 2 | 3 |

| Antibody | Form | Isotype | M | C1 | C2 | Affinity (EA1) | *B. thuringeneisis**** @100ug/ml | |
|---|---|---|---|---|---|---|---|---|
| | | | | | | | Al Hakam | HD571 |
| 1- 9F6 (AX-EA1-G1) | Purified | IgG1 | 3 | 0 | 1 | 3 | 0 | 0 |
| 7- 8G4- 1D7 | Purified | IgG1 | 3 | 0 | 2 | 3 | 0 | 0 |
| 7- 3C3- 2C2 | Purified | IgG1 | 3 | 1 | 1 | 2 | 0 | 0 |
| 7- 1D4- 1G7 | Purified | IgG1 | 3 | 1 | 2 | 2 | 0 | 0 |
| 7- 6B6- 1C9 | Purified | IgG1 | 2 | 0 | 2 | 3 | 0 | 0 |
| 7- 1E10- 1B5 | Purified | IgG1 | 2 | 0 | 2 | 3 | 0 | 0 |
| 7- 9F5- 2B11 | Purified | IgG1 | 3 | 1 | 2 | 3 | 0 | 0 |
| 7- 9C2- 1C11 | Purified | IgG1 | 3 | 1 | 2 | 2 | 0 | 0 |
| 7- 5E4- 1C10 | Purified | IgG1 | 3 | 1 | 1 | 2 | 0 | 0 |
| 7- 8D3- 1E6 | Cell sup | IgG1 | P/M | 0 | 1 | P/M | 0 | 0 |
| 7- 2B11- 1B10 | Cell sup | IgG1 | 3 | P/M | 2 | 2 | 0 | 0 |
| 7- 7E10- 1D8 | Cell sup | IgG1 | P/M | 0 | 1 | 1 | 0 | 0 |
| 7- 9E8- 1B11 | Cell sup | IgG1 | 3 | 1 | 2 | 3 | 0 | 0 |
| 7- 10E8 | Cell sup | IgG1 | 3 | 1 | 2 | 3 | 0 | 0 |

TABLE 1-continued

| | | | \*\*Relative Scoring of ELISA Data Based on 0-3 Scale\* | | | | | |
|---|---|---|---|---|---|---|---|---|
| 7- 1G7- 1A6 | Cell sup | IgG1 | 3 | 1 | 1 | 2 | 0 | 0 |
| 7- 8D7 | Cell sup | IgG1 | 3 | 1 | 2 | 3 | 0 | 0 |

B-Rabbit anti-anthrax (polyclonal)
3 (OD = 1.542)
3 (OD = 2.188)
*0 = negative result; 1-3 = positive result with 3 being the highest titers
**Key to antigen preparations on following page.
***Near neighbor of *B. anthracis*
P/M = Plus/Minus
(+) = Highest Titer in group
Key to Antigen Preparations Evaluated in Table 1
•Sp1 Standard washed spore prepared from plates (Prepare according to procedure from Lot 260400-01, with washes in PBS)
Sp3 fresh spore culture prepared from plates (Wash off spores with dH2O and test by ELISA fresh)
•SpG1 Standard washed spore prepared from modified G (Prepare according to procedure from Lot 210400-01, with washes in PBS)
SpG3 Fresh spore culture prepared from modified G (Test straight from modified G media, once in spore state)
V1 Vegetative cells grown on TSA plates, washed off plates in PBS; 2× centrifuge, resuspend pellet in PBS, freeze
•V + M Vegetative cells in culture media and tested fresh by ELISA; freeze remainder
•M Supernatant without vegetative cells
C1 Control 1 - frozen prep lot 260400-01
C2 Control 2 - frozen prep lot 210400-01
Affinity (EA1)AX-EA1-G1 affinity-purified antigen corresponding to EA1 protein
•Denotes Frozen samples

TABLE 2

Specificity Testing Performance for Anthrax Capture ELISA with
Capture Ab: Rabbit anti Anthrax/Detector Ab: AX-EA1-G1 Mab Positive Controls:

| Antigen Conc | Positive Control (Affinity Pur. Anthrax sterne) | Antigen Conc | Anthrax spore prep (Mod. G) T210400-01 | Antigen Conc CFU/ml | Anthrax sterne spore prep lot T310100-01 |
|---|---|---|---|---|---|
| 50 ug/ml | not tested | 40 ug/ml | 0.889 | 1.00E+05 | 1.596 |
| 25 ug/ml | not tested | 20 ug/ml | 0.809 | 5 00E+04 | 1.278 |
| 12.5 ug/ml | not tested | 10 ug/ml | 0.394 | 2.50E+04 | 0.666 |
| 6.25 ug/ml | 2.810 | 5 ug/ml | 0.214 | 1.25E+04 | 0.312 |
| 3.13 ug/ml | 2.924 | 2.5 ug/ml | 0.088 | 6.25E+03 | 0.177 |
| 1.56 ug/ml | 2.962 | Blank | 0.000 | 3.13E+03 | 0.093 |

**Bacillus thuringensis:*

| Antigen Conc | Bt Dipel Dust spore prep T130201-03 | Bt Dipel Dust veg prep T130201-04 | Bt ATCC 33680 veg T100201-01 | Bt HD571 spore T100400-02 | Bt Al Hakam spore T100400-01 |
|---|---|---|---|---|---|
| 40 ug/ml | 0.000 | 0.026 | 0.000 | 0.013 | 0.000 |
| 20 ug/ml | 0.011 | 0.000 | 0.007 | 0.057 | 0.005 |
| 10 ug/ml | 0.018 | 0.005 | 0.072 | 0.008 | 0.014 |
| 5 ug/ml | 0.000 | 0.015 | 0.005 | 0.000 | 0 017 |
| 2.5 ug/ml | 0.000 | 0.000 | 0.004 | 0.000 | 0.000 |
| Blank | 0.000 | 0.000 | 0.082 | 0.000 | 0.065 |

Other *Bacillus* species:

| Antigen Conc | *B. globigii* spore prep T190100-01 | *B. globigii* veg prep T120100-01 | Antigen Dilution | *B. licheniformis* ATCC 25972 |
|---|---|---|---|---|
| 50 ug/ml | 0.000 | 0.000 | 2N | 0.001 |
| 25 ug/ml | 0.000 | 0.003 | 4N | 0.000 |
| 12.5 ug/ml | 0.004 | 0.000 | 8N | 0.001 |
| 6.25 ug/ml | 0.000 | 0.005 | 16N | 0.000 |
| 3.13 ug/ml | not tested | not tested | 32N | 0.002 |
| 1.56 ug/ml | not tested | not tested | Blank | 0.000 |

| Other Bacteria: | | | Other Proteins and Toxins: | | |
|---|---|---|---|---|---|
| Antigen Conc | *F. tularensis* LVS T300300-01 | *Y. pestis* 11-29-99 | Antigen Conc | Ovalbumin T270200-01 | SEB Sigma 39H4018 |
| 50 ug/ml | 0.007 | 0.002 | 50 ug/ml | 0.004 | 0.000 |
| 25 ug/ml | 0.012 | 0.004 | 25 ug/ml | 0.002 | 0.000 |

TABLE 2-continued

Specificity Testing Performance for Anthrax Capture ELISA with
Capture Ab: Rabbit anti Anthrax/Detector Ab: AX-EA1-G1 Mab

| | | | | | |
|---|---|---|---|---|---|
| 12.5 ug/ml | 0.008 | 0.004 | 12.5 ug/ml | 0.006 | 0.000 |
| 6.25 ug/ml | 0.004 | 0.001 | 6.25 ug/ml | 0.001 | 0.001 |
| 3.13 ug/ml | 0.004 | 0.003 | 3.13 ug/ml | 0.002 | 0.002 |
| 1.56 ug/ml | 0.004 | 0.003 | 1.56 ug/ml | 0.002 | 0.000 |

Misc.

| Antigen Dilution | **Red Clay | **Gravel | **Mulch |
|---|---|---|---|
| 2N | 0.000 | 0.002 | 0.002 |
| 4N | 0.004 | 0.007 | 0.001 |
| 8N | 0.003 | 0.004 | 0.002 |
| 16N | 0.001 | 0.001 | 0.002 |
| 32N | 0.004 | 0.002 | 0.001 |
| 64N | 0.003 | 0.001 | 0.000 |

*Nearest neighbor of *B. anthracis*
**Prepared by adding 0.5 g to 3 ml ELISA buffer; vortex and let settle 15 min before addition to plate
Red highlighted optical density readings are positive results

TABLE 3

Specificity Testing Performance for Anthrax Capture ELISA with Capture Ab: Rabbit anti Anthrax/Detector Ab: 8G4 Mab Positive Controls:

| Antigen Conc | Anthrax spore prep (Mod. G) T210400-01 | Anthrax sterne spore prep lot T290101-01 | Positive Control (Affinity Pur. Anthrax sterne) |
|---|---|---|---|
| 50 ug/ml | 2.763 | 2.603 | 2.645 |
| 25 ug/ml | 2.781 | 2.705 | 2.658 |
| 12.5 ug/ml | 2.786 | 2.686 | 2.519 |
| 6.25 ug/ml | 2.729 | 2.663 | 2.561 |
| 3.13 ug/ml | 2.718 | 2.655 | 2.570 |
| 1.56 ug/ml | not tested | not tested | 2.757 |

**Bacillus thuringensis*:

| Antigen Conc | Bt Dipel Dust spore prep T130201-03 | Bt Dipel Dust veg prep T130201-04 | Bt ATCC 33680 veg T100201-01 | Bt HD571 spore T100400-02 | Bt Al Hakum spore T100400-01 |
|---|---|---|---|---|---|
| 40 ug/ml | 0.001 | 0.002 | 0.020 | 0.027 | 0.024 |
| 20 ug/ml | 0.022 | 0.000 | 0.011 | 0.040 | 0.011 |
| 10 ug/ml | 0.104 | 0.016 | 0.017 | 0.025 | 0.000 |
| 5 ug/ml | 0.001 | 0.000 | 0.017 | 0.000 | 0.033 |
| 2.5 ug/ml | 0.000 | 0.012 | 0.002 | 0.000 | 0.003 |
| Blank | 0.011 | 0.008 | 0.010 | 0.005 | 0.017 |

Other *Bacillus* species:

| Antigen Conc | *B. globigii* spore prep T190100-01 | *B. globigii* veg prep T120100-01 | Antigen Dilution | *B. licheniformis* ATCC 25972 |
|---|---|---|---|---|
| 50 ug/ml | 0.000 | not tested | 2N | 0.001 |
| 25 ug/ml | 0.000 | not tested | 4N | 0.004 |
| 12.5 ug/ml | 0.012 | not tested | 8N | 0 001 |
| 6.25 ug/ml | 0.000 | not tested | 16N | 0 002 |
| 3.13 ug/ml | 0.076 | not tested | 32N | 0 004 |
| 1.56 ug/ml | 0.041 | not tested | Blank | 0 002 |

| Other Bacteria: | | | Other Proteins and Toxins: | | |
|---|---|---|---|---|---|
| Antigen Conc | *F. tularensis* LVS T300300-01 | *Y. pestis* 11-29-99 | Antigen Conc | Ovalbumin T270200-01 | SEB Sigma 89H4018 |
| 50 ug/ml | 0.000 | 0.000 | 50 ug/ml | 0.000 | 0.000 |
| 25 ug/ml | 0.000 | 0.000 | 25 ug/ml | 0.002 | 0.000 |
| 12.5 ug/ml | 0.000 | 0.000 | 12.5 ug/ml | 0.102 | 0.005 |
| 6.25 ug/ml | 0.000 | 0.000 | 6.25 ug/ml | 0.040 | 0.000 |

TABLE 3-continued Specificity Testing Performance for Anthrax Capture ELISA with
Capture Ab: Rabbit anti Anthrax/Detector Ab: 8G4 Mab

| | | | | | |
|---|---|---|---|---|---|
| 3.13 ug/ml | 0.000 | 0.000 | 3.13 ug/ml | 0.111 | 0.004 |
| 1.56 ug/ml | 0.013 | 0.000 | 1.56 ug/ml | 0.061 | 0.003 |

Misc.

| Antigen Dilution | **Red Clay | **Gravel | **Mulch |
|---|---|---|---|
| 2N | 0.000 | 0.000 | 0.000 |
| 4N | 0.000 | 0.038 | 0.013 |
| 8N | hot well | 0.008 | 0.012 |
| 16N | 0.019 | 0.000 | 0.028 |
| 32N | 0.000 | 0.049 | 0.000 |
| 64N | 0.000 | 0.000 | 0.002 |

*Nearest neighbor of *B. anthracis*

**Prepared by adding 0.5 g to 3 ml ELISA buffer, vortex and let settle 15 min before addition to plate Red highlighted optical density readings are positive results

TABLE 4

Specificity Testing Performance for Anthrax Capture ELISA with Capture Ab: Rabbit anti Anthrax/Detector Ab: 9F5 Mab Positive Controls:

| Antigen Conc | Anthrax spore prep (Mod.G) T210400-01 | Anthrax sterne spore prep for T290101-01 | Positive Control (Affinity Pur. Anthrax sterne |
|---|---|---|---|
| 50 ug/ml | 2.885 | 2.927 | 2.284 |
| 25 ug/ml | 2.835 | 2.795 | 2.226 |
| 12.5 ug/ml | 2.891 | 2.807 | 1.834 |
| 6.25 ug/ml | 2.721 | 2.801 | 1.821 |
| 3.13 ug/ml | 2.760 | 2.772 | 1.665 |
| 1.56 ug/ml | 0.000 | 0.009 | 1.539 |

**Bacillus thuringensis:*

| Antigen Conc | Bt Dipel Dust spore prep T130201-03 | Bt Dipel Dust veg prep T130201-04 | Bt ATCC 33680 veg T100201-01 | Antigen Conc | Bt HD571 spore T100400-02 | Bt Al Hakum spore T100400-01 |
|---|---|---|---|---|---|---|
| 50 ug/ml | 0.116 | 0.003 | 0.001 | 100 ug/ml | 0.073 | 0.049 |
| 25 ug/ml | 0.086 | 0.000 | 0.000 | 20 ug/ml | 0.029 | 0.029 |
| 12.5 ug/ml | 0.049 | 0.002 | 0.001 | 4 ug/ml | 0.004 | 0.007 |
| 6.25 ug/ml | 0.064 | 0.000 | 0.000 | Blank | 0.000 | 0.001 |
| 3.13 ug/ml | 0.033 | 0.000 | 0.000 | | | |
| 1.56 ug/ml | 0.045 | 0.000 | 0.001 | | | |

Other *Bacillus* species:

| Antigen Conc | *B. globigii* spore prep T190100-01 | *B. globigii* veg prep T120100-01 | Antigen Dilution | *B. licheniformics* ATCC 25972 |
|---|---|---|---|---|
| 50 ug/ml | 0.000 | not tested | 2N | 0.000 |
| 25 ug/ml | 0.000 | not tested | 4N | 0.000 |
| 12.5 ug/ml | 0.000 | not tested | 8N | 0.002 |
| 6.25 ug/ml | 0.000 | not tested | 16N | 0.003 |
| 3.13 ug/ml | 0.014 | not tested | 32N | 0.000 |
| 1.56 ug/ml | 0.061 | not tested | Blank | 0.000 |

| Other Bacteria: | | | Other Proteins and Toxins: | | |
|---|---|---|---|---|---|
| Antigen Conc | *F. tularensis* LVS T-300300-01 | *Y. pestis* 11-29-99 | Antigen Conc | Ovalbumin T270200-01 | SEB Sigma 89H4018 |
| 50 ug/ml | 0.000 | 0.000 | 50 ug/ml | 0.029 | 0.000 |
| 25 ug/ml | 0.000 | 0.042 | 25 ug/ml | 0.000 | 0.000 |
| 12.5 ug/ml | 0.048 | 0.002 | 12.5 ug/ml | 0.043 | 0.000 |
| 6.25 ug/ml | 0.000 | 0.000 | 6.25 ug/ml | 0.000 | 0.009 |

TABLE 4-continued

Specificity Testing Performance for Anthrax Capture ELISA with
Capture Ab: Rabbit anti Anthrax/Detector Ab: 9F5 Mab

| 3.13 ug/ml | 0.032 | 0.000 | 3.13 ug/ml | 0.030 | 0.013 |
| 1.56 ug/ml | 0 000 | 0.000 | 1 56 ug/ml | 0.008 | 0.000 |

| | Misc. | | |
|---|---|---|---|
| Antigen Dilution | **Red Clay | **Gravel | **Mulch |
| 2N | 0.047 | 0.104 | 0.011 |
| 4N | 0.000 | 0.000 | 0.000 |
| 8N | hot well | 0.000 | 0.009 |
| 16N | 0.012 | 0.000 | 0.006 |
| 32N | 0.026 | 0.000 | 0.001 |
| 64N | 0 079 | 0.000 | 0.000 |

*Nearest neighbor of *B. anthracis*
**Prepared by adding 0.5 g to 3 ml ELISA buffer; vortex and let settle 15 min before addition to plate
Red highlighted optical density readings are positive results

---

The invention claimed is:

1. A diagnostic kit comprising an isolated monoclonal antibody, or a fragment thereof, that
   binds EA1 polypeptide of *B. anthracis,*
   wherein said antibody is produced by a hybridoma deposited with ATCC and accorded accession number PTA-2632.

2. The diagnostic kit of claim 1, further comprising a colloidal particle based lateral flow detection system.

3. The diagnostic kit of claim 1, further comprising a detection system selected from a carbon based lateral flow system; a fluorescent based assay system, a chemiluminescent system, an up converting phosphors system, a refractive indexed based detection system, a magnetic bead or latex bead system, and a micro array system.

4. The diagnostic kit of claim 1, wherein said antibody, or a fragment thereof, does not bind *B. cereus.*

5. The kit of claim 1, wherein said antibody or fragment thereof is *B. anthracis* specific.

6. The kit of claim 1, wherein said antibody or fragment thereof does not bind *B. thuringiensis.*

7. The kit of claim 1, wherein said antibody or fragment thereof binds to SEQ ID NO:1 or an antigenic portion thereof.

8. The kit of claim 1, wherein said antibody or fragment thereof specifically binds *B. anthracis* spores.

9. The kit of claim 1, wherein said antibody or fragment thereof specifically binds *B. anthracis* vegetative cells.

10. The kit of claim 1, wherein said antibody or fragment thereof does not bind *B. globigii.*

11. The kit of claim 1, wherein said fragment is an Fab or Fv fragment.

12. The kit of claim 1, wherein said antibody or fragment thereof specifically binds *B. licheniformis*.

13. An isolated monoclonal antibody, or a fragment thereof, that
binds EA1 polypeptide of *B. anthracis*,
wherein said antibody is produced by a hybridoma deposited with ATCC and accorded accession number PTA-2632.

14. The antibody or fragment thereof of claim 13, wherein said antibody or fragment thereof is *B. anthracis* species specific.

15. The antibody or fragment of claim 13, wherein said antibody or fragment thereof does not bind *B. thuringiensis*.

16. The antibody or fragment thereof of claim 13, wherein said antibody or fragment thereof binds to SEQ ID NO:1 or an antigenic portion thereof.

17. The antibody or fragment thereof of claim 13, wherein said antibody or fragment thereof does not bind *B. cereus*.

18. The antibody or fragment thereof of claim 13, wherein said fragment is an Fab or Fv fragment.

19. A method of detecting *B. anthracis* spores or cells in a sample, said method comprising
contacting a monoclonal antibody, or fragment thereof, with a sample, containing a *B. anthracis* spore or cell, to form a complex comprising said antibody, or fragment, and a *B. anthracis* spore or cell, and
detecting said complex from said sample;
wherein said antibody is produced by a hybridoma deposited with ATCC and accorded accession number PTA-2632 wherein said detection of said coplex indicates the presence of *B. anthracis* spores or cells.

20. The method of claim 19, wherein said antibody or fragment thereof binds EA1 polypeptide of *B. anthracis*.

21. The method of claim 19, wherein said antibody or fragment thereof is *B. anthracis* species specific.

22. The method of claim 19, wherein said antibody or fragment thereof does not bind *B. thuringiensis*.

23. The method of claim 19, wherein said antibody or fragment thereof binds to SEQ ID NO:1 or an antigenic portion thereof.

24. The method of claim 19, wherein said antibody or fragment thereof does not bind *B. cereus*.

25. The method of claim 19, wherein said fragment is an Fab or Fv fragment.

26. The method of claim 19, wherein said antibody or fragment thereof does not bind *B. licheniformis*.

27. The method of claim 19, wherein said contacting comprises a colloidal particle based lateral flow detection system.

28. The method of claim 19, wherein said detecting comprises a detection system selected from a carbon based lateral flow system; a fluorescent based assay system, a chemiluminescent system, an up converting phosphors system, a refractive indexed based detection system, a magnetic bead or latex bead system, and a micro array system.

29. The method of claim 19, wherein said complex comprises a *B. anthracis* spore.

30. The method of claim 19, wherein said complex comprises a *B. anthracis* vegetative cell.

31. The method of claim 19, wherein said antibody or fragment thereof does not bind *B. globigii*.

* * * * *

SEQUENCE LISTING

<160> NUMBER OF SEQ ID NOS: 3

<210> SEQ ID NO 1
<211> LENGTH: 833
<212> TYPE: PRT
<213> ORGANISM: Bacillus anthracis

<400> SEQUENCE: 1

```
Ala Gly Lys Ser Phe Pro Asp Val Pro Ala Gly His Trp Ala Glu Gly
1               5                   10                  15

Ser Ile Asn Tyr Leu Val Asp Lys Gly Ala Ile Thr Gly Lys Pro Asp
            20                  25                  30

Gly Thr Tyr Gly Pro Thr Glu Ser Ile Asp Arg Ala Ser Ala Ala Val
        35                  40                  45

Ile Phe Thr Lys Ile Leu Asn Leu Pro Val Asp Glu Asn Ala Gln Pro
    50                  55                  60

Ser Phe Lys Asp Ala Lys Asn Ile Trp Ser Ser Lys Tyr Ile Ala Ala
65                  70                  75                  80

Val Glu Lys Ala Gly Val Val Lys Gly Asp Gly Lys Glu Asn Phe Tyr
                85                  90                  95

Pro Glu Gly Lys Ile Asp Arg Ala Ser Phe Ala Ser Met Leu Val Ser
            100                 105                 110

Ala Tyr Asn Leu Lys Asp Lys Val Asn Gly Glu Leu Val Thr Thr Phe
        115                 120                 125

Glu Asp Leu Leu Asp His Trp Gly Glu Glu Lys Ala Asn Ile Leu Ile
    130                 135                 140

Asn Leu Gly Ile Ser Val Gly Thr Gly Gly Lys Trp Glu Pro Asn Lys
145                 150                 155                 160

Ser Val Ser Arg Ala Glu Ala Ala Gln Phe Ile Ala Leu Thr Asp Lys
                165                 170                 175

Lys Tyr Gly Lys Lys Asp Asn Ala Gln Ala Tyr Val Thr Asp Val Lys
            180                 185                 190

Val Ser Glu Pro Thr Lys Leu Thr Leu Thr Gly Thr Gly Leu Asp Lys
        195                 200                 205

Leu Ser Ala Asp Asp Val Thr Leu Glu Gly Asp Lys Ala Val Ala Ile
    210                 215                 220
```

-continued

```
Glu Ala Ser Thr Asp Gly Thr Ser Ala Val Val Thr Leu Gly Gly Lys
225                 230                 235                 240
Val Ala Pro Asn Lys Asp Leu Thr Val Lys Val Lys Asn Gln Ser Phe
                245                 250                 255
Val Thr Lys Phe Val Tyr Glu Val Lys Lys Leu Ala Val Glu Lys Leu
            260                 265                 270
Thr Phe Asp Asp Arg Ala Gly Gln Ala Ile Ala Phe Lys Leu Asn
        275                 280                 285
Asp Glu Lys Gly Asn Ala Asp Val Glu Tyr Leu Asn Leu Ala Asn His
    290                 295                 300
Asp Val Lys Phe Val Ala Asn Asn Leu Asp Gly Ser Pro Ala Asn Ile
305                 310                 315                 320
Phe Glu Gly Gly Glu Ala Thr Ser Thr Thr Gly Lys Leu Ala Val Gly
                325                 330                 335
Ile Lys Gln Gly Asp Tyr Lys Val Glu Val Gln Val Thr Lys Arg Gly
                340                 345                 350
Gly Leu Thr Val Ser Asn Thr Gly Ile Ile Thr Val Lys Asn Leu Asp
            355                 360                 365
Thr Pro Ala Ser Ala Ile Lys Asn Val Val Phe Ala Leu Asp Ala Asp
        370                 375                 380
Asn Asp Gly Val Val Asn Tyr Gly Ser Lys Leu Ser Gly Lys Asp Phe
385                 390                 395                 400
Ala Leu Asn Ser Gln Asn Leu Val Val Gly Glu Lys Ala Ser Leu Asn
                405                 410                 415
Lys Leu Val Ala Thr Ile Ala Gly Glu Asp Lys Val Val Asp Pro Gly
                420                 425                 430
Ser Ile Ser Ile Lys Ser Ser Asn His Gly Ile Ile Ser Val Val Asn
            435                 440                 445
Asn Tyr Ile Thr Ala Glu Ala Ala Gly Glu Ala Thr Leu Thr Ile Lys
    450                 455                 460
Val Gly Asp Val Thr Lys Asp Val Lys Phe Lys Val Thr Thr Asp Ser
465                 470                 475                 480
Arg Lys Leu Val Ser Val Lys Ala Asn Pro Asp Lys Leu Gln Val Val
                485                 490                 495
Gln Asn Lys Thr Leu Pro Val Thr Phe Val Thr Thr Asp Gln Tyr Gly
            500                 505                 510
Asp Pro Phe Gly Ala Asn Thr Ala Ala Ile Lys Glu Val Leu Pro Lys
        515                 520                 525
Thr Gly Val Val Ala Glu Gly Gly Leu Asp Val Val Thr Thr Asp Ser
    530                 535                 540
Gly Ser Ile Gly Thr Lys Thr Ile Gly Val Thr Gly Asn Asp Val Gly
545                 550                 555                 560
Glu Gly Thr Val His Phe Gln Asn Gly Asn Gly Ala Thr Leu Gly Ser
                565                 570                 575
Leu Tyr Val Asn Val Thr Glu Gly Asn Val Ala Phe Lys Asn Phe Glu
            580                 585                 590
Leu Val Ser Lys Val Gly Gln Tyr Gly Gln Ser Pro Asp Thr Lys Leu
        595                 600                 605
Asp Leu Asn Val Ser Thr Thr Val Glu Tyr Gln Leu Ser Lys Tyr Thr
    610                 615                 620
Ser Asp Arg Val Tyr Ser Asp Pro Glu Asn Leu Glu Gly Tyr Glu Val
625                 630                 635                 640
Glu Ser Lys Asn Leu Ala Val Ala Asp Ala Lys Ile Val Gly Asn Lys
```

-continued

```
                    645                 650                 655
Val Val Val Thr Gly Lys Thr Pro Gly Lys Val Asp Ile His Leu Thr
                660                 665                 670

Lys Asn Gly Ala Thr Ala Gly Lys Ala Thr Val Glu Ile Val Gln Glu
                675                 680                 685

Thr Ile Ala Ile Lys Ser Val Asn Phe Lys Pro Val Gln Thr Glu Asn
                690                 695                 700

Phe Val Glu Lys Lys Ile Asn Ile Gly Thr Val Leu Glu Leu Glu Lys
705                 710                 715                 720

Ser Asn Leu Asp Asp Ile Val Lys Gly Ile Asn Leu Thr Lys Glu Thr
                725                 730                 735

Gln His Lys Val Arg Val Val Lys Ser Gly Ala Glu Gln Gly Lys Leu
                740                 745                 750

Tyr Leu Asp Arg Asn Gly Asp Ala Val Phe Asn Ala Gly Asp Val Lys
                755                 760                 765

Leu Gly Asp Val Thr Val Ser Gln Thr Ser Asp Ser Ala Leu Pro Asn
                770                 775                 780

Phe Lys Ala Asp Leu Tyr Asp Thr Leu Thr Thr Lys Tyr Thr Asp Lys
785                 790                 795                 800

Gly Thr Leu Val Phe Lys Val Leu Lys Asp Lys Asp Val Ile Thr Ser
                805                 810                 815

Glu Ile Gly Ser Gln Ala Val His Val Asn Val Leu Asn Asn Pro Asn
                820                 825                 830

Leu

<210> SEQ ID NO 2
<211> LENGTH: 12
<212> TYPE: PRT
<213> ORGANISM: Bacillus anthracis

<400> SEQUENCE: 2

Ala Gly Lys Glx Phe Pro Glx Val Pro Ala Gly His
1               5                   10

<210> SEQ ID NO 3
<211> LENGTH: 12
<212> TYPE: PRT
<213> ORGANISM: Bacillus anthracis

<400> SEQUENCE: 3

Asp Glx Lys Glx Asn Ala Gln Ala Tyr Val Thr Asp
1               5                   10
```